(12) United States Patent  
Krauss

(10) Patent No.: US 8,542,230 B2  
(45) Date of Patent: Sep. 24, 2013

(54) METHOD FOR PREPARING CT IMAGE DISPLAYS, AND AN ARITHMETIC LOGIC UNIT FOR CARRYING OUT THIS METHOD

(75) Inventor: Bernhard Krauss, Burgthann (DE)

(73) Assignee: Siemens Aktiengesellschaft, Munich (DE)

( * ) Notice: Subject to any disclaimer, the term of this patent is extended or adjusted under 35 U.S.C. 154(b) by 682 days.

(21) Appl. No.: 12/725,946

(22) Filed: Mar. 17, 2010

(65) Prior Publication Data

US 2010/0238171 A1    Sep. 23, 2010

(30) Foreign Application Priority Data

Mar. 19, 2009   (DE) .................. 10 2009 014 051

(51) Int. Cl.
   *G06T 17/00*        (2006.01)
(52) U.S. Cl.
   USPC .......................................................... 345/424
(58) Field of Classification Search
   USPC .......................................................... 345/424
   See application file for complete search history.

(56) References Cited

U.S. PATENT DOCUMENTS

| 2007/0217570 A1 | 9/2007 | Grasruck et al. | |
| 2008/0253508 A1 * | 10/2008 | Krauss | 378/19 |

FOREIGN PATENT DOCUMENTS

| DE | 102006009222 A1 | 9/2007 |
| DE | 102007017629 A1 | 10/2008 |
| WO | WO 2005076222 A1 | 8/2005 |

OTHER PUBLICATIONS

Robert E. Alvarez and A. Macovski; Energy-selective reconstructions in X-ray computerised tomography Alvarez et al.; Phys. Med. Biol. 21 733-744; Others; 1976.

Bolotin H. H.; "Analytic and quantitative exposition of patient-specific systematic inaccuracies inherent in planar DXA-derived in vivo BMD measurements"; Medical Physics; vol. 25; No. 2; 1998; AU; pp. 139-151.

* cited by examiner

*Primary Examiner* — Edward Martello  
(74) *Attorney, Agent, or Firm* — Harness, Dickey & Pierce, P.L.C.

(57) ABSTRACT

A method is disclosed for preparing CT image displays. In at least one embodiment, the method includes compiling $N \geq 2$ CT image data records of an area of a patient on the basis of N different X-ray energy spectra, each pixel or voxel being assigned an N-tuple CT numbers, each CT number of the N-tuple being assigned to the absorption value of one of the N X-ray energy spectra; carrying out material destruction over at least one predetermined subarea of the area of the patient represented in the CT image data records with reference to at least three materials including at least bone mineral, yellow bone marrow and red bone marrow; and outputting and/or displaying at least one CT image data record at least with reference to the predetermined subarea with absorption values relating to one of the N X-ray energy spectra or to a mathematically simulated spectrum from which the bone mineral content is extracted.

22 Claims, 3 Drawing Sheets

FIG 4
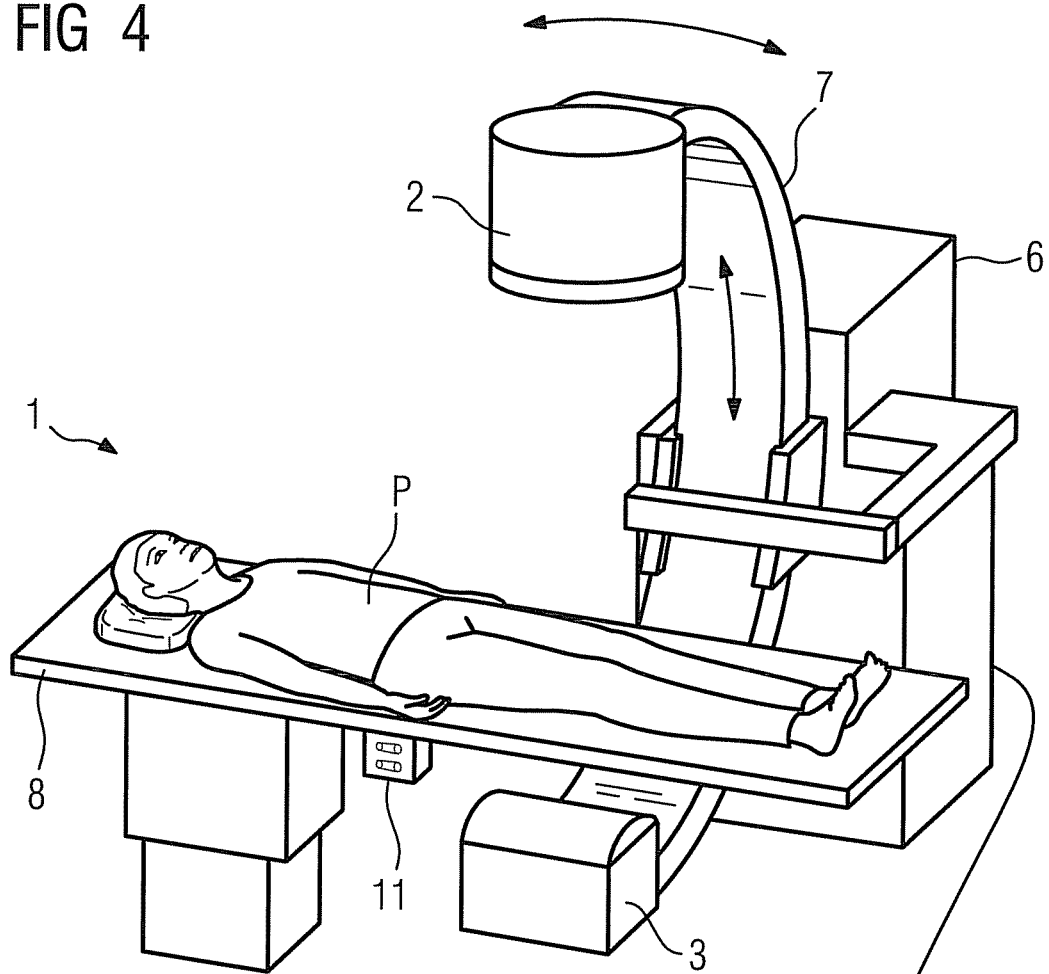
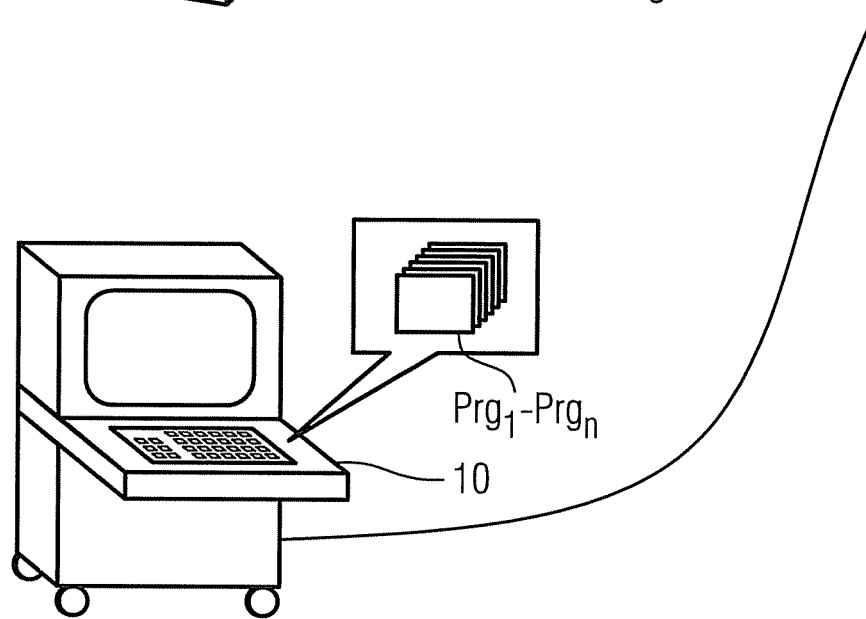

METHOD FOR PREPARING CT IMAGE DISPLAYS, AND AN ARITHMETIC LOGIC UNIT FOR CARRYING OUT THIS METHOD

PRIORITY STATEMENT

The present application hereby claims priority under 35 U.S.C. §119 on German patent application number DE 10 2009 014 051.4 filed Mar. 19, 2009, the entire contents of which are hereby incorporated herein by reference.

FIELD

At least one embodiment of the invention generally relates to a method for preparing CT image displays that are generated by the scanning of a patient with the aid of a CT system on the basis of at least two different X-ray energy spectra, and/or to an arithmetic logic unit for carrying out this method.

BACKGROUND

Methods for scanning patients with the aid of two or more X-ray energy spectra and/or with the aid of energy resolving detectors are generally known. It is also known in principle that such scanning methods can be used to prepare CT image displays in such a way that it is possible to detect different materials in CT image data records. In particular, these methods are used in order to render contrast agent or calcium detectable even in low doses, and/or to quantify concentration thereof.

However, if the aim is to detect a necrotic or an edematous change in the bone marrow such as frequently occurs, for example, in sports injuries, neither the CT image nor the possibly calculated calcium or soft tissue content permits a conclusion on the state of the bone marrow. For this reason, the diagnosis of bone marrow edemas in conjunction with possible bone fractures currently requires both that patients be subjected to examination in a single spectrum or multispectra CT system in order to find bone fractures, that is to say damage in the mineral structure of the bone, and that a magnetic resonance tomography examination be carried out in which bone marrow edemas possibly present become detectable.

SUMMARY

In at least one embodiment of the invention, a method is disclosed for preparing CT image displays from multienergy CT examinations in the case of which it is possible, in addition to displaying the bone structures for the purpose of diagnosing fractures, also to detect edemas or necrosis in bone marrow on the basis of a single examination.

The inventor has recognized that the substantial obstacle to the detection of bone marrow edemas in CT image displays resides in the fact that the relatively slight changes in absorption owing to edematous changes in the bone marrow are generally overlaid by the neighboring, strongly visible bone structure such that said changes can scarcely be detected because of partial volume effects. Consequently, the visibility of bone marrow edemas in CT image displays can be substantially improved by masking bone mineral components in the image display in CT image data records. This requires the pixels or voxels to be illustrated in the display with the pixel or voxel values that are changed in such a way that the optical impression of a bone marrow edema is no longer overlaid by bone mineral components. This can be done by a mathematical extraction of the mineral induced absorption components in the context of a material decomposition. A 2-material decomposition into bone mineral and residual tissue, however, does not lead to the desired result in this case.

In accordance with the findings of the inventor, the desired display result can be achieved only by a decomposition into at least 3 materials, specifically bone mineral, red bone marrow and yellow bone marrow. However, when extracting the absorption induced by bone mineral from the pixel or voxel values, it should be ensured that volume components of bone mineral that have been removed are refilled by the remaining material, in which case their ratios to one another should be maintained. A normalization should therefore be carried out.

If the absorption component produced by bone mineral, that is to say by the bone structure is removed in a way according to the invention, the result is an image impression that also visualizes relatively small differences in the absorption in the region of the bone marrow, and also shows edematous changes.

In accordance with the abovedescribed finding of the inventor, the latter proposes a method for preparing CT image displays having the following method steps:

compiling $N \geq 2$ CT image data records of an area of a patient on the basis of N different X-ray energy spectra, each pixel or voxel being assigned an N-tuple of CT numbers, each CT number of the N-tuple being assigned to the absorption value of one of the N X-ray energy spectra, carrying out material decomposition over at least one predetermined subarea of the area of the patient represented in the CT image data records with reference to at least three materials including at least bone mineral, yellow bone marrow and red bone marrow, and outputting and/or displaying at least one CT image data record at least with reference to the predetermined subarea with absorption values relating to one of the N X-ray energy spectra or to a mathematically simulated spectrum from which the bone mineral content is extracted.

The dominating impression of pixels and voxels that have predetermined calcium components is drastically reduced, up to being cancelled, in the displayed CT image data record owing to this measure, and so the eye can even detect slight differences in CT values that result from the incorporation of fluid into the bone marrow, that is to say through bone marrow edemas. In a special variant of the inventive method, use is made of the fact that the CT values of yellow bone marrow, red bone marrow and any desired mixtures thereof change approximately by the same absolute value when bone mineral of the concentration c is embedded therein.

In order to determine the volume components of the materials of yellow bone marrow and red bone marrow of the entire bone marrow volume and the concentration of the bone mineral, use can be made here of the following energy-dependent equation, and the solution of a system of equations is calculated per pixel or voxel:

$$x(E) = g \times x_{gelb}(E) + r \times x_{rot}(E) + c \times \Delta x_{Km}(E), \text{ where } r = (1-g), \text{ and:}$$

x(E) corresponds to the measured absorption value with reference to the energy spectrum E, g corresponds to the volume component of the yellow bone marrow of the bone marrow, $x_{gelb}(E)$ corresponds to the absorption value of yellow bone marrow with reference to the energy spectrum E, r corresponds to the volume component of the red bone marrow of the bone marrow, $x_{rot}(E)$ corresponds to the absorption value of red bone marrow with reference to the energy spectrum E, c corresponds to the concentration of the bone mineral, and $\Delta x_{Km}(E)$ corresponds to the change in the absorption value of bone marrow per concentration of the bone mineral with reference to the energy spectrum E.

The pixel or voxel values output in this case can be calculated in accordance with the following formula:

$$x_A(E) = g \times x_{gelb}(E) + (1-g) \times x_{rot}(E)$$

where $x_A(E)$ is the output absorption value relating to the energy spectrum E. In this equation, it is also possible to use for $x_{gelb}$ and $x_{rot}$ values that correspond to one another (not measured) spectrum. Since it is assumed in this variant of the calculation of the pixel and/or voxel values extracted from bone mineral, that the bone mineral effects the same incremental change in the absorption for all possible bone marrow mixtures, it is possible to dispense with a subsequent normalization of the actual volume components.

In accordance with another variant, which is a closer approach to reality, of the method, it is proposed furthermore, that in the case of the material decomposition the volume components are determined for each of the three materials of bone mineral, yellow bone marrow and red bone marrow. In order to determine these volume components, it is possible here to use the following energy-dependent equation, and to calculate the solution of a system of equations per pixel or voxel with the following equation:

$$x(E) = g \times x_{gelb} + r \times x_{rot} + k \times x_{Km}, \text{ where } r = 1 - g - k \text{ and:}$$

$x(E)$ corresponds to the measured absorption value with reference to the energy spectrum E, g corresponds to the volume component of the yellow bone marrow, $x_{gelb}$ corresponds to the absorption value of yellow bone marrow with reference to the energy spectrum E, r corresponds to the volume component of red bone marrow, $x_{rot}$ corresponds to the absorption value of red bone marrow with reference to the energy spectrum E, k corresponds to the volume component of bone minerals and $x_{Km}$ corresponds to the absorption value of bone mineral with reference to the energy spectrum E.

In the case of this last named variant of the method, the respectively output pixel or voxel values can be calculated on the assumption that the pixel or voxel consists exclusively of the materials of yellow and red bone marrow, the relationship of the determined volume components being maintained. According to the invention, this can be done by virtue of the fact that the output pixel or voxel values are calculated and normalized in accordance with the following formula:

$$x_A(E) = \frac{g}{1-k} \times x_{gelb}(E) + \frac{1-k-g}{1-k} \times x_{rot}(E),$$

where $x_A(E)$ is the output absorption value in relation to the energy spectrum E. In this equation, it is possible in turn to make use for $x_{gelb}$ and $x_{rot}$ of values that correspond to another (not measured) spectrum. Here, a pixel or voxel value is output that corresponds to an absorption value in the case of which a respective pixel or voxel replaces the bone mineral proportionately with reference to the residual materials. Such an illustration then corresponds in principle to a display of the CT image in the case of which any bone mineral has been virtually extracted from the CT image data record such that it is now more easily possible to detect even relatively small differences in the gray-scale values because of the substantially reduced dynamics in the gray-scale values. In addition, such pictures can be provided artificially with greater dynamics range such that even relatively small differences stand out more strongly to the human eye. It is standard practice for such image displays to be illustrated in gray-scale values with reference to their absorption values.

According to at least one embodiment of the invention, it is additionally possible to scale the calculated absorption value linearly or nonlinearly in relation to each pixel or voxel, and to display it in addition to another image for example a CT image. For example, this can be done by an additional coloring of the pixels, the size of the distance from yellow bone marrow being capable of expression by a different coloring or by a degree of coloring of the respective pixel. Since edematous bone marrow is generally remote from the line between yellow bone marrow and bone mineral inside the absorption value diagram, it is hereby possible to detect with particular clarity an area specifically in the extremities that is changed edematously.

As already described at the beginning, a predetermined subarea is particularly to be treated in accordance with at least one embodiment of the inventive method in the display of a CT image. It is particularly advantageous here when the area of a bone is selected as predetermined subarea, it being possible for this subarea to be determined automatically, for example by a segmentation. It is then possible either to exclusively display the selected subarea that has been processed according to at least one embodiment of the invention, or to select an image combination between a normal CT image and a bone illustration—in accordance with at least one embodiment of the inventive method.

According to at least one embodiment of the invention, the previously described method can be executed both on the basis of conventional dual energy CT pictures or multienergy CT pictures, such pictures being subject to all the problems of a beam hardening in the image, in particular in the area of recorded bones. It is therefore particularly advantageous when the method described here is also carried out on the basis of at least two CT displays that were respectively calculated by simulating a monochromatic radiation from originally measured raw data. Hardening artifacts can be avoided completely in the case of such a simulation, that is to say a virtual generation of a CT image on the basis of a monochromatic radiation, or else of a predetermined narrow energy spectrum.

As mentioned at the beginning, the method described here is particularly well suited to displaying extremities of a patient, it being possible here to output either 2-dimensional CT image data records or 3-dimensional CT image data records.

In addition to the above-described inventive method, the framework of at least one embodiment of the invention also includes an arithmetic logic unit, in particular an arithmetic logic unit of a CT system, the unit being intended to contain a memory with program code that executes the method steps of the above-described method during operation of the arithmetic logic unit.

BRIEF DESCRIPTION OF THE DRAWINGS

The invention is described in more detail below with reference to an example embodiment and with the aid of figures, only the features required to understand the invention being illustrated, and use being made of the following reference symbols: 1: CT system/C-arc system; 2: first X-ray tube; 3: first detector; 4: second X-ray tube (optional); 5: second detector system (optional); 6: gantry housing/C-arc drive; 7:

C-arc; 8: movable patient couch; 9: system axis; 10: control and arithmetic logic unit; 11: contrast agent applicator; P: patient; $Prg_1$-$Prg_n$: computer programs; I to IV: method steps.

Figure 1:
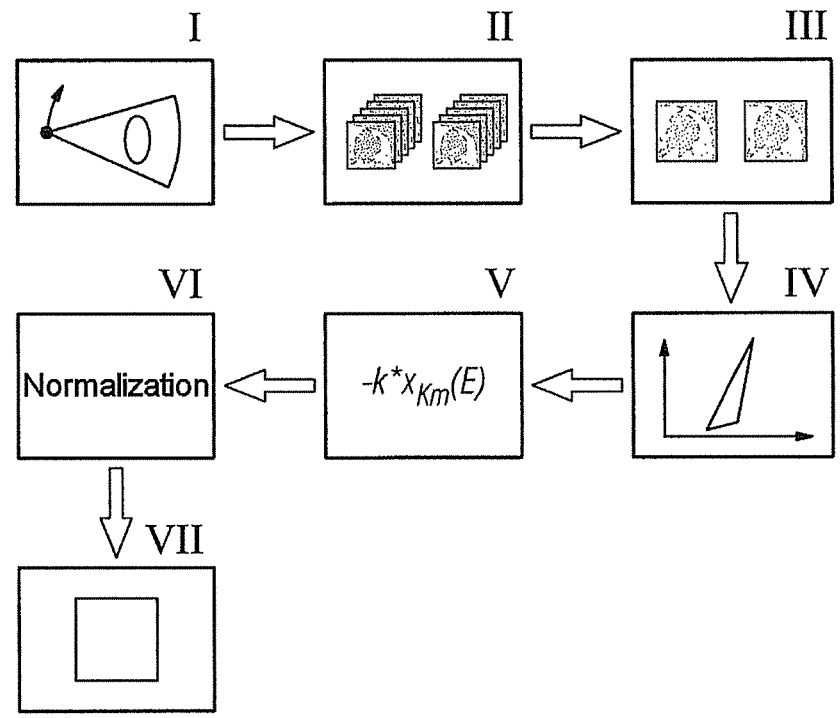
Figure 2:
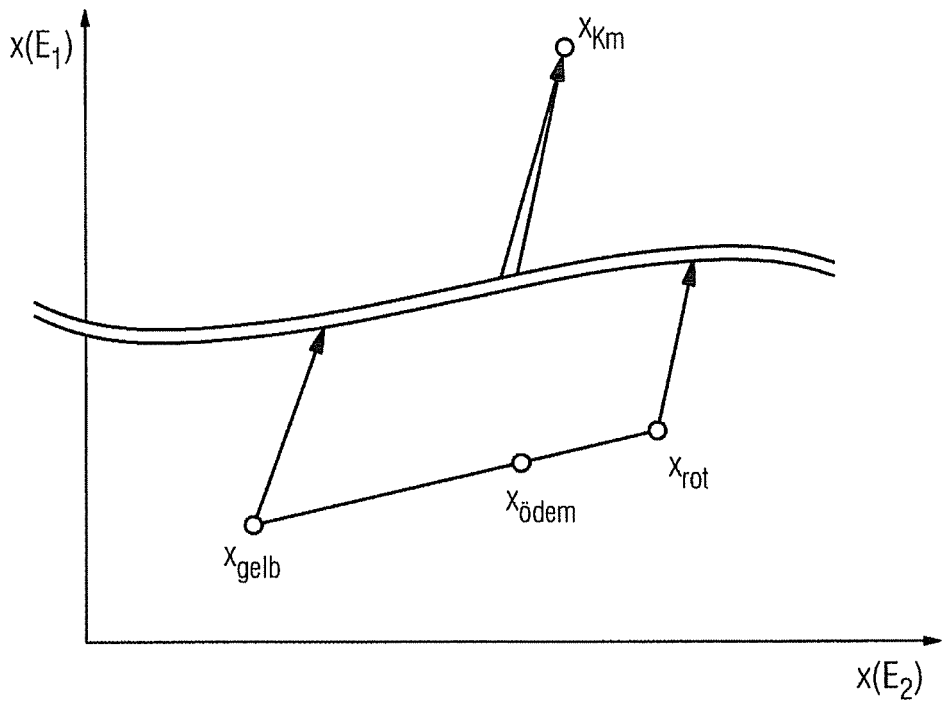
Figure 3:
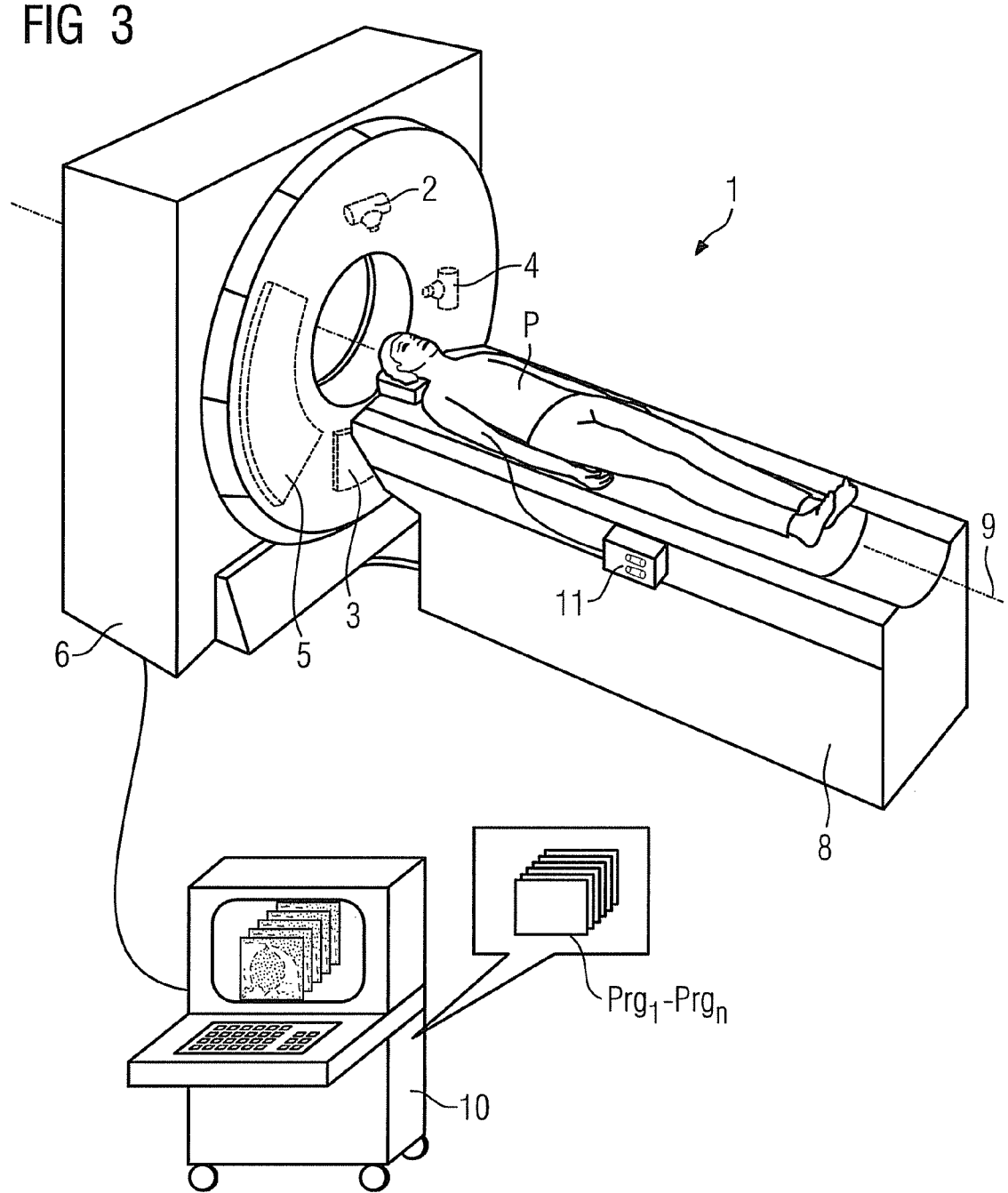

In detail:

FIG. 1 shows a schematic of the course of an embodiment of the inventive method, FIG. 2 shows a schematic of the material decomposition in the CT values diagram of two X-ray spectra, FIG. 3 shows a CT system for carrying out an embodiment of the inventive method, and FIG. 4 shows a C-arc system for carrying out an embodiment of the inventive method.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a schematic of the course of an embodiment of the inventive method in seven method steps. A patient is scanned in the first method step I. This can be done, for example, by a dual energy scan in which scanning is performed serially with two different energy spectra or simultaneously with the aid of tube/detector systems, or by switching over quickly between two acceleration voltages during scanning. Alternatively, it is also possible to use an energy-selective detector system in conjunction with the use of a single X-ray spectrum for irradiation of the patient.

In method step II, the scanning data thus determined are used to produce two image data records whose absorption data relates respectively to different X-ray energy spectra or X-ray energy values. There now follows in method step III a selection of the image area viewed, for example by a segmentation of the recorded bone, and thereupon in method step IV a material decomposition known per se, at least the volume components of yellow and red bone marrow being calculated, preferably also the volume component of the bone mineral. There then follows in method step V the extraction of the absorption component of bone mineral with the subsequent normalization of the remaining volume components in method step VI. After completion of normalization, the correspondingly changed pixel or voxel values are illustrated in method step VII such that the viewing medical staff are presented with an optimized display in which edematous changes in the bone marrow in the area of bones can be assessed particularly well.

FIG. 2 illustrates once again the carrying out of the material decomposition with the aid of a CT values diagram. Here, the CT values $x(E_1)$ are plotted on the ordinate with reference to a first energy spectrum, while the CT values $x(E_2)$ are plotted on the abscissa with reference to a second energy spectrum. Each pixel or voxel of a CT image display is thus given a tuple of CT values that can be plotted in this diagram. The mutually matching CT value tuple with reference to yellow bone marrow with $x_{gelb}$ red bone marrow with $x_{rot}$ and bone mineral $x_{Km}$ are plotted in this illustration. Since the absorption of bone mineral is substantially greater than the absorption of yellow or red bone marrow, the ordinate is represented with a break. A typical absorption value for edematous bone marrow is shown with CT value $x_{ödem}$ on the connecting line between $x_{gelb}$ and $x_{rot}$.

Looking now at the determined CT values from two CT image displays of the same object corresponding to two different energy spectra or energy regions $E_1$ and $E_2$, there results for each pixel in accordance with the respective volume component g and r of yellow and red bone marrow of the total bone marrow and a concentration c of bone mineral the following system of equations that is to be solved:

$$x(E_1) = g \times x_{gelb}(E_1) + r \times x_{rot}(E_1) + c \times \Delta x_{Km}(E_1)$$

$$x(E_2) = g \times x_{gelb}(E_2) + r \times x_{rot}(E_2) + c \times \Delta x_{Km}(E_2)$$

c being independent of g, and it being assumed that $\Delta x_{Km} \propto x_{Km} - x_g$, which is only approximately correct for red bone marrow. By definition, it also holds that $r=(1-g)$, and so it holds that:

$$x(E_1) = g \times x_{gelb}(E_1) + (1-g) \times x_{rot}(E_1) + c \times \Delta x_{Km}(E_1)$$

$$x(E_2) = g \times x_{gelb}(E_2) + (1-g) \times x_{rot}(E_2) + c \times \Delta x_{Km}(E_2)$$

It is thus thereby possible to use two absorption values with reference to a pixel to calculate the concentration c of the bone mineral and the volume component g of the yellow bone marrow including the complementary volume component of the red bone marrow on the basis of two different energy regions. If the component of the absorption of the bone mineral is now subtracted from the measured absorption value, the result is an absorption value that reproduces only the yellow and red bone marrow.

An improved way of viewing the real situation is provided by the following system of equations;

$$x(E_1) = g \times x_{gelb}(E_1) + r \times x_{rot}(E_1) + k \times x_{Km}(E_1)$$

$$x(E_2) = g \times x_{gelb}(E_2) + r \times x_{rot}(E_2) + k \times x_{Km}(E_2).$$

Here, each material—yellow bone marrow, red bone marrow and bone mineral—is assigned a dedicated volume component g, r and k. Proceeding from the assumption that the materials specified here are exclusively to hand, it holds that $1=(r+g+k)$ and thus $r=(1-g-k)$ and therefore that the following system of equations:

$$x(E_1) = g \times x_{gelb}(E_1) + (1-g-k) \times x_{rot}(E_1) + k \times x_{Km}(E_1)$$

$$x(E_2) = g \times x_{gelb}(E_2) + (1-g-k) \times x_{rot}(E_2) + k \times x_{Km}(E_2)$$

This system of equations can therefore also be used to calculate the respective volume component of the materials with reference to two energy ranges from the knowledge of two absorption values per pixel or voxel, and thus also to subtract the absorption component of the bone mineral from the measured values. If the volume component of the bone mineral is thus eliminated, the remainder of the volume components must again be normalized to 1 such that it holds for the CT values without bone mineral components which are to be displayed that:

$$x_A(E) = \frac{g}{1-k} \times x_{gelb}(E) + \frac{1-k-g}{1-k} \times x_{rot}(E),$$

it being possible to use the respectively selected energy region $E_1$ or $E_2$ for E.

It may be further mentioned that the values $x_{gelb}(E_i)$, $x_{rot}(E_i)$, $x_{Km}(E_i)$ specified here correspond to the respective typical CT values in the case of the corresponding energy with reference to yellow and red bone marrow and bone mineral.

The inventive method of an embodiment can be carried out, for example, with the aid of the CT system 1 such as is illustrated in FIG. 3. In such a CT system 1, a patient P is located on a movable couch 8 and can be pushed during a scan with the aid of this movable couch 8 through an open measurement field inside a gantry. Located on this gantry is an X-ray tube 2, illustrated schematically here, with a detector 3 opposite, optionally also a second X-ray tube 4 with an optional second detector 5. A multi-energy scan can be carried out in the known way with the aid of this one or these two tube/detector system(s), the control of the actual scan being performed by the arithmetic logic and control unit 10 with the aid of the programs $Prg_1$ to $Prg_n$ stored therein.

It is also possible to use an energy-selective detector as an alternative to scanning with a plurality of X-ray spectra. The measured absorptions can hereby be split up in an energy specific fashion and two or more CT absorption displays can be correspondingly produced with reference to different X-ray energies or spectra.

The determined energy-specific CT displays can then be used, on the one hand, to display the bone structure in order to assess possibly existing fractures, and to carry out a material decomposition on the basis of the same examination in accordance with the inventive method described above, and to conduct a display without bone mineral for the purpose of diagnosing bone marrow edemas.

If desired, it is also possible in addition to administer a contrast agent via a contrast agent applicator 11 such that other desired organic structures can be better detected.

As an alternative to the CT system from FIG. 3,

FIG. 4 shows a C-arc system 1 in which a patient P is likewise located on a patient couch 8. The tube/detector system with the X-ray tube 2 and the opposite detector 3 is located here on a C-arc 7 that, under the control of the control and arithmetic logic unit 10, can be pivoted about the patient in order to scan the patient through a rotational angle of at least 180°, in order in this way to obtain reconstructible absorption data of the patient. It is preferred in the present case to use a detector 3 that operates in an energy selective fashion such that it is possible to use a single X-ray tube to reconstruct CT displays that are based on different X-ray energy spectra.

Embodiments of the inventive methods can be carried out with the aid of the computer programs $Prg_1$ to $Prg_n$ present in the control and arithmetic logic unit 10, such that it is possible to output on a display unit, for example, the control and arithmetic logic unit 10 itself, a CT image display in the case of which on the one hand bone structures can be effectively detected while, on the other hand, a better detection of bone marrow edemas is possible by removing the absorptions specific to bone mineral.

Although it is advantageously possible in principle to carry out this preparation of the CT image data records directly on a CT system or C-arc system, it is nevertheless also possible to make use for this purpose of a separate arithmetic logic unit to which the CT image data are transmitted for further processing.

It goes without saying that the features of the invention that are named above can be used not only in the respectively specified combination, but also in other combinations or on their own without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for preparing CT image displays, comprising:
   compiling CT image data records of an area of a patient on the basis of $N \geq 2$ different X-ray energy spectra, each pixel or voxel of the CT image data records being assigned an N-tuple of CT numbers, each CT number of the N-tuple being assigned to an absorption value of one of the N different X-ray energy spectra;
   carrying out material decomposition over at least one subarea of the area of the patient represented in the CT image data records with reference to at least three materials including at least bone mineral, yellow bone marrow and red bone marrow; and
   at least one of outputting and displaying at least one CT image data record at least with reference to the subarea with absorption values relating to one of the N different X-ray energy spectra or to a mathematically simulated spectrum from which the bone mineral content is extracted.

2. The method as claimed in claim 1, wherein the carrying out material decomposition determines an equal CT value change for yellow and red bone marrow if a first concentration of bone mineral exists, and
   at least volume fractions of the yellow bone marrow and red bone marrow relative to a total volume of bone marrow, and the concentration of bone mineral are determined.

3. The method as claimed in claim 2, wherein, in order to determine the volume fractions of the yellow bone marrow and red bone marrow and the concentration of the bone mineral, use is made of the following energy-dependent equation, and the solution of a system of equations is calculated per pixel or voxel:

$$x(E) = g \times x_{gelb}(E) + r \times x_{rot}(E) + c \times \Delta x_{Km}(E) \text{ where } r = (1-g)$$
and:

x(E) corresponds to a measured absorption value with reference to the energy spectrum E,
g corresponds to a volume component of yellow bone marrow on the bone marrow,
$x_{gelb}(E)$ corresponds to an absorption value of yellow bone marrow with reference to the energy spectrum E,
r corresponds to a volume component of red bone marrow on the bone marrow, $x_{rot}(E)$ corresponds to an absorption value of red bone marrow with reference to the energy spectrum E, c corresponds to a concentration of the bone mineral, and $\Delta x_{Km}(E)$ corresponds to an increase in the absorption value of bone marrow per concentration of the bone mineral with reference to the energy spectrum E.

4. The method as claimed in claim 3, wherein output pixel or voxel values are calculated in accordance with the following formula:

$$x_A(E) = g \times x_{gelb}(E) + (1-g) \times x_{rot}(E)$$

where $x_A(E)$ is an output absorption value relating to the energy spectrum E.

5. The method as claimed in claim 1, wherein, in the case of the material composition, volume fractions are determined for each of the three materials of bone mineral, yellow bone marrow and red bone marrow.

6. The method as claimed in claim 5, wherein, in order to determine the volume fractions of the bone mineral, yellow bone marrow and red bone marrow, use is made of the following energy-dependent equation, and the solution of a system of equations is calculated per pixel or voxel:

$$x(E) = g \times x_{gelb} + r \times x_{rot} + k \times x_{Km}, \text{ where } r = 1-g-k \text{ and:}$$

$x(E)$ corresponds to a measured absorption value with reference to the energy spectrum E, g corresponds to a volume component of the yellow bone marrow, $x_{gelb}$ corresponds to an absorption value of yellow bone marrow with reference to the energy spectrum E, r corresponds to a volume component of red bone marrow, $x_{rot}$ corresponds to an absorption value of red bone marrow with reference to the energy spectrum E, k corresponds to a volume component of bone minerals and $x_{Km}$ corresponds to an absorption value of bone mineral with reference to the energy spectrum E.

7. The method as claimed in claim 5, wherein, in the case of output pixel or voxel values, the output value is calculated on the assumption that the pixel or voxel consists exclusively of the materials of yellow and red bone marrow, the relationship of the determined volume fractions being maintained.

8. The method as claimed in claim 6, wherein output pixel or voxel values are calculated and normalized in accordance with the following formula:

$$x_A(E) = \frac{g}{1-k} \times x_{gelb}(E) + \frac{1-k-g}{1-k} \times x_{rot}(E),$$

where $x_A(E)$ is an output absorption value in relation to the energy spectrum (E).

9. The method as claimed in claim 1, wherein, with reference to their absorption values, output pixel or voxel values are represented in gray-scale values.

10. The method as claimed in claim 9, wherein the output pixel or voxel values are rescaled linearly or nonlinearly.

11. The method as claimed in claim 10, wherein the rescaled pixel or voxel values is displayed by different coloration of the pixel or voxel.

12. The method as claimed in claim 1, wherein the subarea is comprised exclusively of bone.

13. The method as claimed in claim 12, wherein the subarea comprising bone is determined on the basis of a segmentation.

14. The method as claimed in claim 1, wherein the method is carried out on the basis of at least two CT displays that were respectively calculated by simulating a monochromatic radiation from originally measured raw data.

15. The method as claimed in claim 1, wherein at least one extremity is selected as the scanned area of the patient.

16. The method as claimed in claim 1, wherein a 2-dimensional CT image data record is output.

17. The method as claimed in claim 1, wherein a 3-dimensional CT image data record is output.

18. An arithmetic logic unit, comprising:
a memory with program code, the program code executing the method steps as claimed in claim 1 when executed and being stored in the memory.

19. The method as claimed in claim 6, wherein, in the case of output pixel or voxel values, the output value is calculated on the assumption that the pixel or voxel consists exclusively of the materials of yellow and red bone marrow, the relationship of the determined volume fractions being maintained.

20. The method as claimed in claim 7, wherein output pixel or voxel values are calculated and normalized in accordance with the following formula:

$$x_A(E) = \frac{g}{1-k} \times x_{gelb}(E) + \frac{1-k-g}{1-k} \times x_{rot}(E),$$

where $x_A(E)$ is an output absorption value in relation to the energy spectrum (E).

21. A CT system comprising the arithmetic logic unit of claim 18.

22. A non-transitory computer readable medium including program segments for, when executed on a computer device, causing the computer device to implement the method of claim 1.

* * * * *